(12) United States Patent
Lockhart et al.

(10) Patent No.: US 9,963,242 B1
(45) Date of Patent: May 8, 2018

(54) MOUNTABLE SENSOR FOR AN AIRCRAFT

(71) Applicants: Mary Lockhart, Fairfax Station, VA (US); Thomas Wallace, Arlington, VA (US); Randal Brumbaugh, Altadena, CA (US); Malcolm Robbie, Stow, OH (US); Brian Patterson, Centennial, CO (US); Donna Blake, Oakton, VA (US); Andreas Goroch, Salinas, CA (US)

(72) Inventors: Mary Lockhart, Fairfax Station, VA (US); Thomas Wallace, Arlington, VA (US); Randal Brumbaugh, Altadena, CA (US); Malcolm Robbie, Stow, OH (US); Brian Patterson, Centennial, CO (US); Donna Blake, Oakton, VA (US); Andreas Goroch, Salinas, CA (US)

(73) Assignee: Blue Storm Associates, Inc., Fairfax Station, VA (US)

( * ) Notice: Subject to any disclaimer, the term of this patent is extended or adjusted under 35 U.S.C. 154(b) by 666 days.

(21) Appl. No.: 14/264,266

(22) Filed: Apr. 29, 2014

(51) Int. Cl.
*G01K 13/00* (2006.01)
*G01K 1/00* (2006.01)
*B64D 43/00* (2006.01)
*G01N 25/56* (2006.01)
*G01L 7/00* (2006.01)

(52) U.S. Cl.
CPC ............ *B64D 43/00* (2013.01); *G01K 13/00* (2013.01); *G01L 7/00* (2013.01); *G01N 25/56* (2013.01)

(58) Field of Classification Search
USPC ................. 374/143, 142, 138, 148, 135, 208
See application file for complete search history.

(56) References Cited

U.S. PATENT DOCUMENTS

| | | | | | |
|---|---|---|---|---|---|
| 2,137,394 | A | * | 11/1938 | Driscoll ................. | B64D 15/16 244/134 D |
| 3,512,414 | A | * | 5/1970 | Rees Patrick .......... | G01K 13/02 244/134 R |
| 4,279,153 | A | * | 7/1981 | Kervistin ............... | G01K 13/02 374/138 |
| 4,710,095 | A | * | 12/1987 | Freberg ................. | F01D 17/085 374/138 |
| 5,457,630 | A | * | 10/1995 | Palmer .................... | B64C 13/50 180/116 |

(Continued)

OTHER PUBLICATIONS

Daniels, Taumi S., et al. "Tropospheric airborne meteorological data reporting (TAMDAR) sensor development." (2004) (available at www.crh.noaa.gov/tamdar/papers/TAMDARsensor.pdf).

(Continued)

*Primary Examiner* — Mirellys Jagan
(74) *Attorney, Agent, or Firm* — Davidson Berquist Jackson and Gowdey, LLP (57) ABSTRACT

A sensor system runs real-time software on the processor to receive and log temperature and humidity data from the sensors. A processor processes the data, reformats, if necessary, the data packaged with GPS information provided by the centralized sensor control system, transmits the packaged data (including error checking) to a designated receiver, and provides a diagnostic interface for displaying logged data and status information. This data is time stamped and transmitted to the centralized sensor control system across the external control/data interface.

19 Claims, 6 Drawing Sheets

(56) References Cited

U.S. PATENT DOCUMENTS

| | | | |
|---|---|---|---|
| 5,460,041 A * | 10/1995 | Andes | G01N 25/64 374/148 |
| 5,796,612 A * | 8/1998 | Palmer | B64C 13/50 244/12.1 |
| 6,270,253 B1 * | 8/2001 | Keller | G01K 1/12 374/138 |
| 6,412,731 B1 | 7/2002 | Gabriel | |
| 6,941,806 B2 | 9/2005 | Burns et al. | |
| 6,974,250 B2 * | 12/2005 | Severson | G01K 13/028 374/138 |
| 7,177,785 B2 | 2/2007 | Hartmann et al. | |
| 7,760,084 B2 | 7/2010 | Jensen et al. | |
| 8,100,582 B1 * | 1/2012 | Powell | G01K 13/028 374/138 |
| 9,465,019 B2 | 10/2016 | Lockhart et al. | |
| 9,725,160 B2 * | 8/2017 | Golling | B64C 21/025 |
| 2002/0122459 A1 * | 9/2002 | McFarland | G01K 1/12 374/179 |
| 2002/0131474 A1 * | 9/2002 | Suga | G01K 13/028 374/138 |
| 2010/0253567 A1 | 10/2010 | Factor et al. | |
| 2011/0038394 A1 * | 2/2011 | Ma | F02D 41/1446 374/148 |
| 2013/0041614 A1 * | 2/2013 | Shepard | G01J 5/0014 702/130 |
| 2013/0163636 A1 * | 6/2013 | Parsons | G01K 13/028 374/158 |
| 2014/0064330 A1 * | 3/2014 | Agami | G01K 13/028 374/138 |
| 2015/0103864 A1 * | 4/2015 | Schwie | B64F 1/26 374/148 |
| 2015/0241286 A1 * | 8/2015 | Isebrand | G01K 13/028 374/138 |
| 2015/0377718 A1 * | 12/2015 | Eichen | G01K 1/14 374/148 |
| 2017/0106585 A1 * | 4/2017 | Nino | G01F 1/46 |
| 2017/0225804 A1 * | 8/2017 | Hafenrichter | B64F 5/0045 |

OTHER PUBLICATIONS

Panasonic Weather Solutions (PWS): Predicting and Reporting In-Flight Icing (Feb. 25, 2015).

* cited by examiner

MOUNTABLE SENSOR FOR AN AIRCRAFT

GOVERNMENT LICENSE RIGHTS

This invention was made with government support under contract W911QY-12-D-0010 (subcontract SC111902-011) awarded by the Department of Defense. The government has certain rights in the invention.

CROSS REFERENCE TO CO-PENDING APPLICATION

This application is related to non-provisional application Ser. No. 14/011,454 filed Aug. 27, 2013, the contents of which are incorporated herein by reference.

FIELD OF INVENTION

The present invention is directed to mountable sensors in aircraft, and, in one embodiment, to a mountable temperature and relative humidity sensor for use with remotely piloted aircraft (RPA).

DISCUSSION OF THE BACKGROUND

Known remotely piloted aircraft currently have limited resource protection in that their environmental/atmospheric sensors are inadequate to detect certain conditions that put the asset (i.e., the RPA) in danger from environmental/atmospheric conditions.

BRIEF DESCRIPTION OF THE DRAWINGS

The following description, given with respect to the attached drawings, may be better understood with reference to the non-limiting examples of the drawings, wherein.

DISCUSSION OF THE PREFERRED EMBODIMENTS

Figure 1:
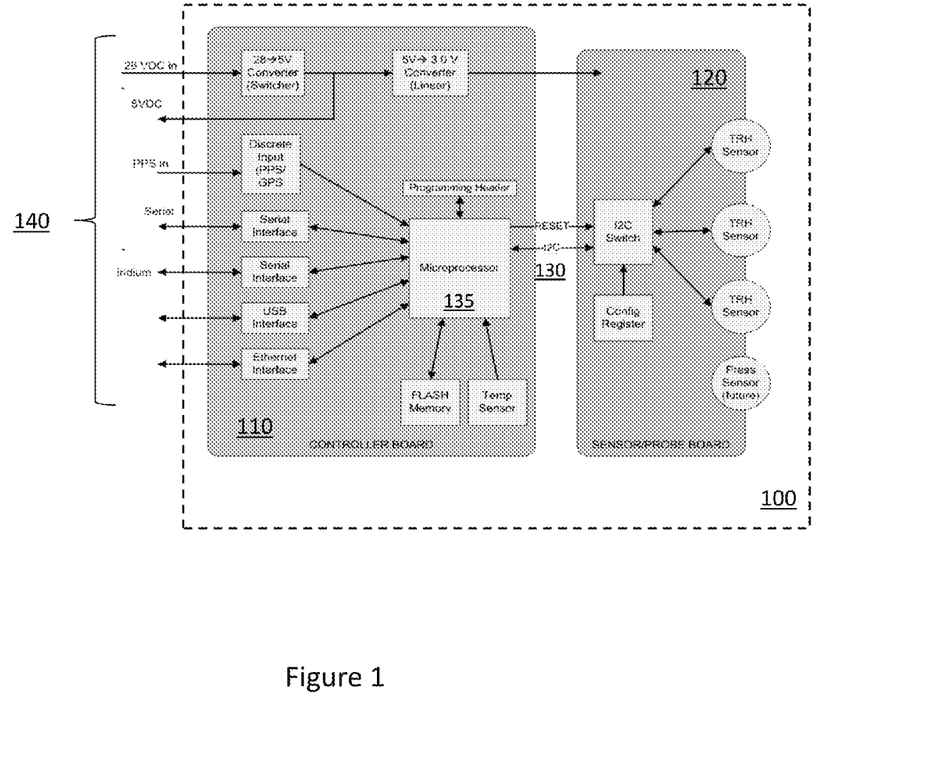
FIG. 1 is block diagram of a sensor system for use with an aircraft.

Turning to FIG. 1, an exemplary sensor system 100 is illustrated in which a sensor control system 110 interacts through an external control/data interface 140 (having one or more ports) while performing environmental/atmospheric sensing to aid in the protection of aircraft (including remotely piloted aircraft (RPA)), such as airplanes and helicopters. In the illustrated embodiment, at least a first port of the external control/data interface 140 (e.g., an Ethernet interface) is connected to a GPS receiver to provide GPS data to the sensor control system 110. However, in an alternate embodiment, the sensor control system 110 may instead include an integrated GPS receiver to enable the sensor control system 110 to be more self-contained. The external control/data interface 140 may include a second port, which may be the same as or different than the first port, for storing data from the sensor control system 110 to a data storage system (e.g., via a data logging process shown in FIG. 8). The external control/data interface 140 may include a third port, which may be the same as or different than the first and second ports, for connecting the sensor control system 110 to an externally connected computer (e.g., a centralized sensor control system for data retrieval, programming and/or debugging). The first and third ports (e.g., for connecting to the data storage system and the externally connected computer) may be custom interfaces or any one or more of various standard data transfer interfaces (e.g., serial interfaces (such as USB, USB 2.0, USB 3.0, $I^2C$, or Thunderbolt), parallel interfaces, wired-network interfaces (e.g., Ethernet) or wireless network interfaces (e.g., any of the 802.11 family of protocols)). The second port for connecting to a data storage system (e.g., a non-volatile memory such as a Flash memory) may be a custom interface or any one or more of various standard data transfer interfaces (e.g., interfaces for removable flash memory cards (such as SD, SDHC, MemoryStick, or CompactFlash), serial interfaces (such as USB, USB 2.0, USB 3.0, $I^2C$, or Thunderbolt), parallel interfaces, wired-network interfaces (e.g., Ethernet) or wireless network interfaces (e.g., any of the 802.11 family of protocols)). The sensor control system 110 may alternatively receive the GPS location information from a centralized sensor control system instead of utilizing a separate connection to the system 110. Any of the first through third ports may supply power to the sensor control system 110, or the sensor system may be connected to power via a power adapter, or the sensor system may be self-powered (e.g., battery powered). In an exemplary embodiment, power (e.g., 28V) is provided from an external source to ensure a controlled voltage source that is common to multiple instruments/sensors which are each connected to the centralized sensor control system.

Figure 8:
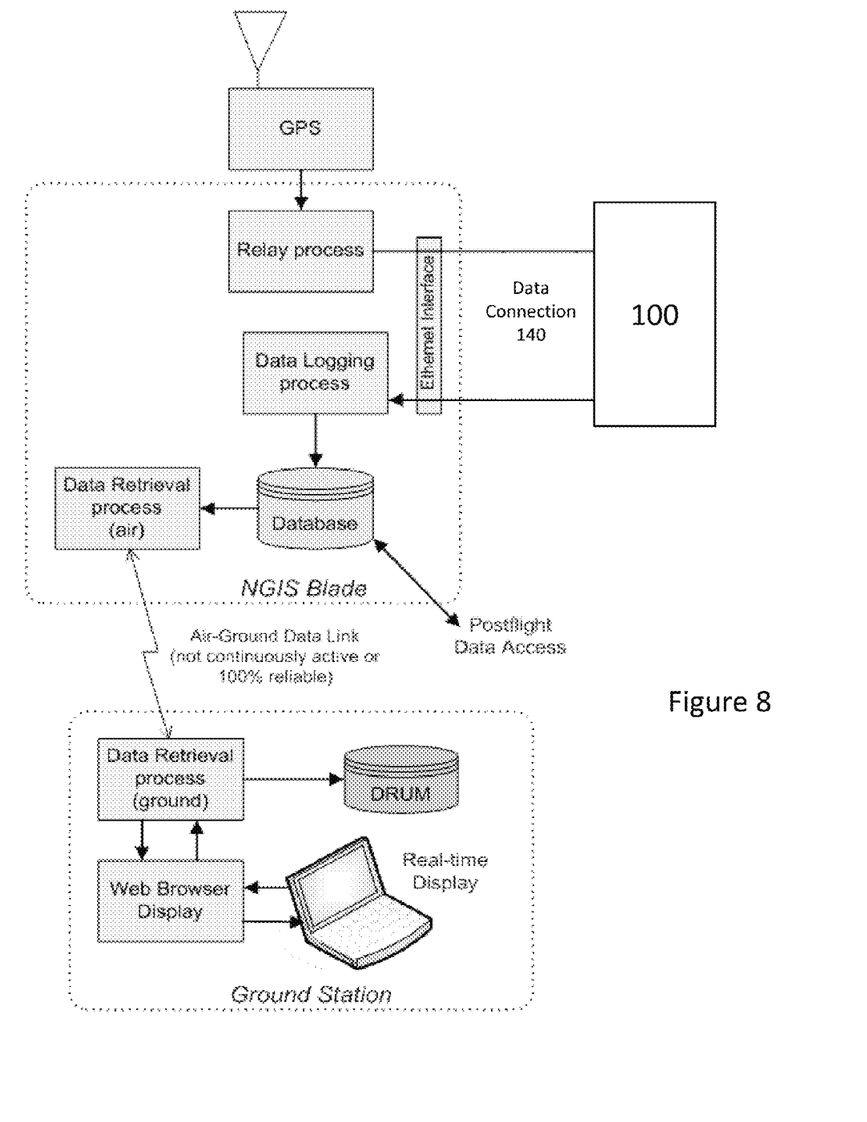
FIG. 8 is a block diagram of an environment using a sensor system for use with an aircraft.

As shown in FIGS. 1 and 8, the sensor control system 110 may be constructed from a number of interconnected sub-components; however, the sensor control system 110 may alternatively have one or more of the sub-components integrated into fewer or more parts than shown. In addition to the sensor control system 110, the system 100 includes a sensor module 120 which includes a number of temperature and relative humidity sensors (TRH sensors) and a pressure sensor, although additional types of sensors could also be provided. The number of TRH sensors may be chosen based on certain design criteria related to an actual environment of use of the sensor control system 110, but three TRH sensors will be described herein without a loss of generality.

As shown in FIG. 1, the TRH sensors are configured such that their data (or a subset of their data) can be sent via the external control/data interface 140 for analysis and/or storage. The exemplary embodiment of FIG. 1 utilizes a microprocessor and its corresponding memory (not shown) in the sensor control system 110 to interface to an $I^2C$ switch in the sensor module 120 to handle the data acquisition and pre-processing before passing the subset of the data to the external control/data interface 140. However, a single processor or several processors also could be utilized instead. For example, the microprocessor, $I^2C$ switch and interface 140 could be built together in a system-on-a-chip (SOC).

The external control/data interface 140 may be connected to a centralized sensor control system that collects real-time data from a number of sensor systems (as shown in FIG. 8). For example, the centralized sensor control system may be a SmartNode Pod from Northrup Grumman, and the data sent from the sensor system 100 would then be configured to send a subset of the data using a protocol and format understood by the SmartNode Pod. Similarly, in such a configuration, the communications link (e.g., Ethernet cable) between the external control/data interface 140 and the centralized sensor control system would be a link that is compatible with a connection to the SmartNode Pod. (As used herein, a "subset" of the sensor data may be a proper subset that includes all of the sensor data.)

As shown in the exemplary embodiment of FIG. 1, a number of TRH sensors utilizing digital outputs are connected to an I²C switch which is used to transfer sensor data to the microprocessor. However, in an alternative embodiment, the TRH sensors may be analog sensors and the sensor module 120 may further include additional circuitry for performing voltage and protocol translation from the physical interface of the TRH sensors to the digital format utilized for subsequent processing internal to the sensor control system 110. For example, the additional circuitry may perform digital-to-analog conversion of analog TRH sensor outputs. The I²C switch may further perform buffering of data from the sensors and control of the sensors (and additional types of sensors, not shown). Such control of the sensors may include calibrations to control or adjust the readings of the sensors during bench testing, ground testing and/or in-flight testing/configuration.

The sensor module 120 may include a configuration register (1) for configuring the I²C switch to control the sensors (e.g., by controlling the number and/or type of sensors connected to sensor control system 110 and/or controlling the frequency of reading of certain sensor information) and/or (2) for identifying the sensor module 120 (e.g., using a unique identifier that can be read from the sensor module 120 by the sensor control system 110). By being able to separately identify sensor modules 120, the sensor control system 110 can work with a number of different sensor modules 120 and dynamically reconfigure how the sensor control system 110 reads data and controls the connected sensors.

Preferably, the TRH sensors simultaneously measure humidity, pressure and temperature for calibration and consistency of data and are small enough to eliminate (or significantly reduce) the thermal inertia problem limiting response time of sensor. Data sampling is further constrained so that reading from the sensors does not cause an increase in the temperature of the sensors themselves. Exemplary sensing intervals are one measurement per second, but faster or slower rates are possible.

As described above, digital outputs are preferably used to minimize crosstalk and other signal quality issues, either by the TRH sensor outputting a digital value directly or by a processor performing analog-to-digital conversion prior to communicating with the sensor control system 110. Further, the use of multiple sensors provides redundancy and aids in calibration of individual sensors. To reduce noise further, the sensor module 120 may further include a dedicated low-voltage power supply, provided through a linear voltage regulator.

The data from the sensor module 120 is then transmitted to the sensor control module 110 across either an internal bus (e.g., I²C) or an external data transfer interface. Some external data transfer interfaces may allow the TRH sensors and the sensor module to be separated from the control processor 135 by a larger physical distance (e.g., 10', 20', or more) than available for an internal bus. This may enable a wider range of placements of the various portions of the sensor control system 110 in order to meet design parameters. For example, the TRH sensors and sensor module may be placed in a first housing that is separate from a second housing of the control processor such that only the first housing is partially exposed to atmospheric/environmental conditions (e.g., by being partially mounted through the exterior of the SmartNode Pod) while the second housing remains mounted inside the SmartNode Pod. This reduces a cross section of the portion of the sensor system that is exposed to the airflow of the aircraft and reduces drag. When utilizing an external data transfer interface, the external data transfer interface can be a custom interface or any one or more of various standard data transfer interfaces (e.g., serial interfaces (such as USB, USB 2.0, USB 3.0, I²C, or Thunderbolt), parallel interfaces, wired-network interfaces (e.g., Ethernet) or wireless network interfaces (e.g., any of the 802.11 family of protocols)).

The use of an externally connectable interface between the sensor control system 110 and the sensor module 120 may further allow quick access to their respective circuitry for field testing, diagnostics and data download. For example, the externally connectable interface can be used by a diagnostic laptop to access the control processor 135 and request that previously stored data or logs be transferred, that diagnostics be run in-field or that software be updated. Similarly, the externally connectable interface may be connected to the sensor module to allow testing of the sensors or reloading of software on the sensor module. Alternatively, the externally connectable interface may include a splitter which enables either the sensor module or another processor to communicate with the processor 135 over the same interface.

As described generally above, the sensor system 100 performs the computations needed for outgoing messages, and formats and sends these messages according to the schedule and method specified in the configuration options. Exemplary message types/formats include, but are not limited to, raw data, processed data, and Cursor on Target (CoT) messages. Preferably all outgoing raw and processed data messages are stored in nonvolatile memory (e.g., NAND flash memory) in the sensor control module 110 for later analysis and/or playback. All aspects of the transmission of each of the three types of messages (enabled/disabled, transmission rate, unicast or multicast mode, destination IP, destination port, and TTL for multicast) can be independently specified in the configuration options.

Raw data messages are simple UDP packets containing data and status information from each of the three sensors, the time and date, and the controller's unique ID. When a raw message is scheduled to be sent, the most recent valid temperature, pressure and relative humidity measurements from each of the three sensors are collected, a calculated dew point temperature, along with the most recent status of the sensors, and the message containing that information is sent to the destination specified in the configuration options.

Processed data messages are UDP packets containing a mean or median temperature and relative humidity computed from all the valid raw measurements received within a specified time window, a calculated dew point temperature and integrated pressure measurements along with time, date, location, wind speed and direction, altitude, heading, and status. The processing method can be chosen using the configuration options to be the mean of all valid measurements, or the median. The mean provides the most accurate estimate of the measured quantity when all the sensors are functioning correctly, while the median will continue to provide useful results even if one sensor has failed completely. The length of the time window for processing is also adjustable using the system options.

Cursor on Target (CoT) messages are XML messages sent as UDP packets. The time, location, temperature, and humidity data in the CoT message are computed in the same way as for processed data. In addition, CoT messages can contain data computed from these measurements. The current CoT implementation computes dew point temperature, probability of icing indicators, and probability of cloud indicators from the processed data.

Figure 2:
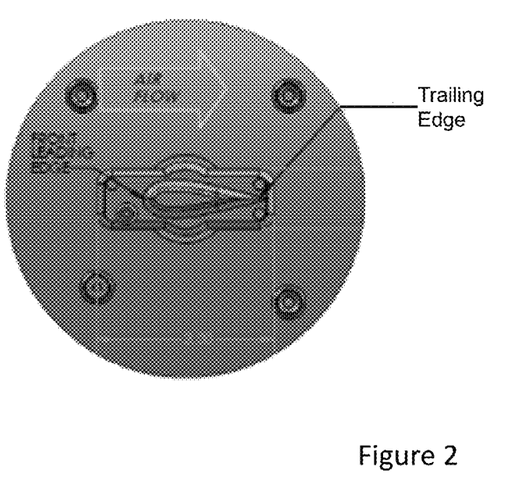
FIG. 2 is a side view of a portion of a sensor housing in an exemplary mounted position.
Figure 3:
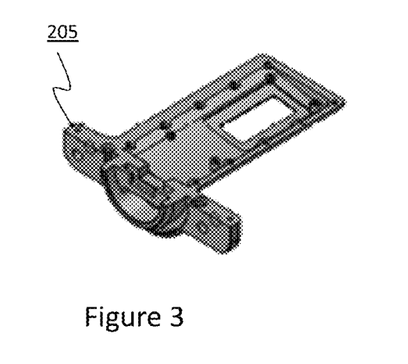
FIG. 3 is a perspective view of a first half of the wing portion of the sensor housing of FIG. 2.
Figure 4:
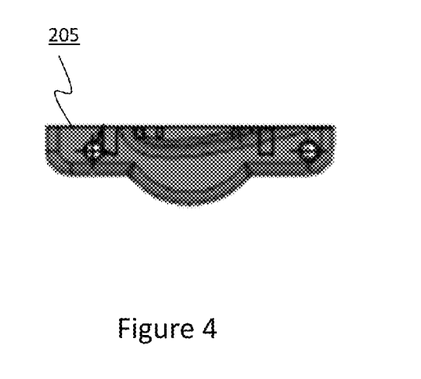
FIG. 4 is a side view of a first half of the wing portion of the sensor housing of FIG. 2.

As shown in FIG. 2, an exemplary sensor housing 200, composed of a number of pieces, surrounds the TRH sensors and the sensor module. Preferably the sensor housing 200 is in the form of an airfoil that surrounds the circuitry and sensors of the sensor module 120 while allowing air to pass into the sensor housing 200. As shown in FIG. 2, air flows over the sensor housing 200 from a front leading edge to a trailing edge. In the configuration of FIG. 2, the sensor housing 200 is connected externally to the RPA and air flows left-to-right. FIG. 3 shows a perspective view of the lower portion 205 of the sensor housing 200, and FIG. 4 shows a side view of the same lower portion, as will be discussed below in greater detail with respect to FIG. 5.

Figure 5:
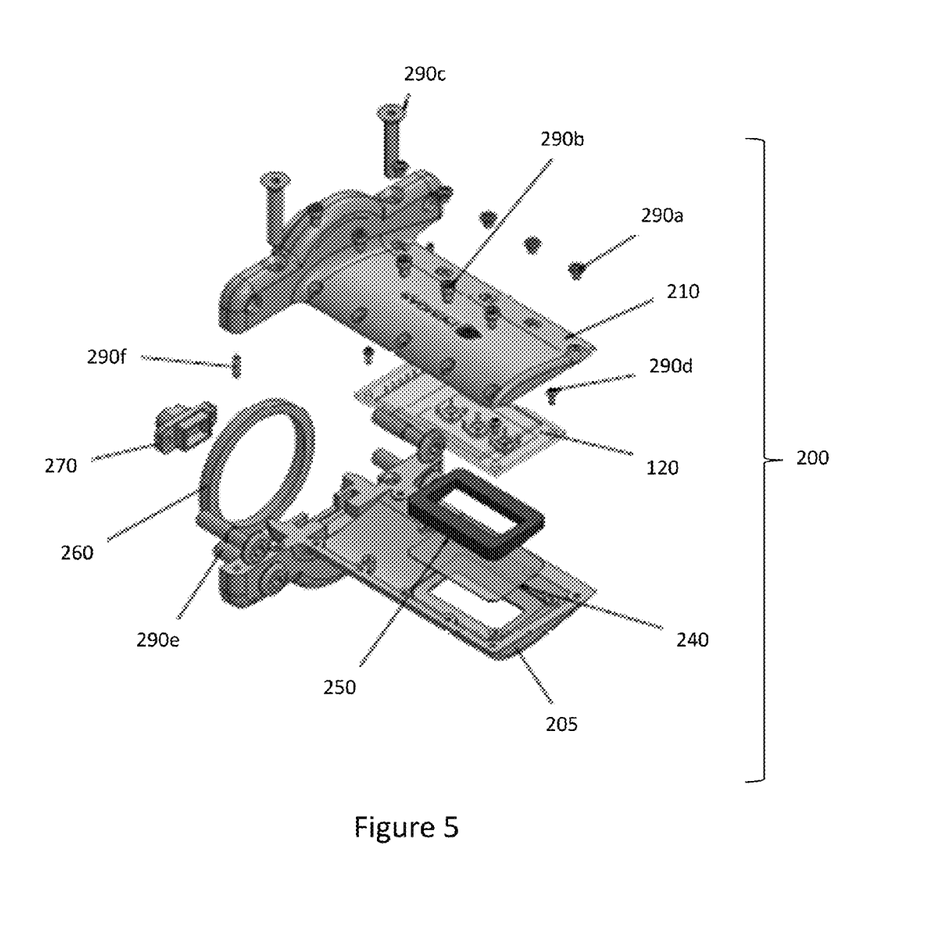
FIG. 5 is an exploded view of the sensor housing and sensor module of FIG. 2.
Figure 9:
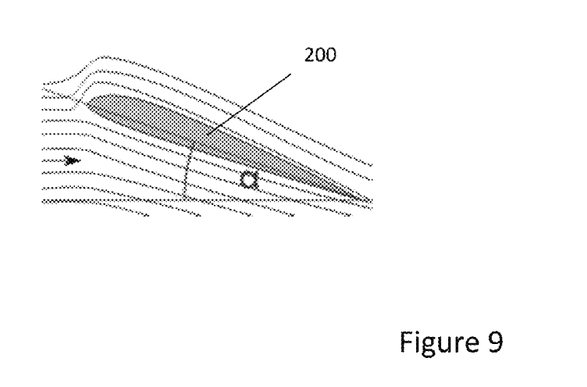
FIG. 9 is a schematic diagram showing an angle-of-attack a between the center reference line of the sensor housing and normal airflow.

As shown in FIG. 5, the sensor housing 200 for the sensor module 120 is assembled from a number of pieces that can be sealed and/or fastened together (e.g., using a series of screws 290a-f of one or more sizes and/or dimensions). The housing is preferably made of heat resistant material (e.g., titanium) which can withstand heat build-up from air friction during flight as well as vibrations and stress. Sandwiched between the lower portion 205 and the upper portion 210 are a number of elements, including, for example, the sensor module 120 (and its associated circuitry and sensors), an air permeable wire mesh 240 and a seal 250 for securely holding the mesh 240 against a back side of the lower portion 205. The lower portion 205 includes an opening (e.g., a rectangular opening) which is covered by the mesh 240 to prevent entry of obstructive material such as bugs, dirt, and ice and to shield the electronics of the sensor module 120 from direct airflow impingement. The mesh 240 allows ambient air molecules to enter the sensor module 120 where measurements for temperature and relative humidity occur. Preferably, the sensor(s) of the sensor module 120 operate(s) with airflow parallel to the housing 200 to minimize airflow through the opening from impinging directly on the sensor(s). Normal flight operations with less than twenty degrees angle-of-attack a (i.e., the angle between the center reference line of the sensor housing 200 and normal airflow, as shown in FIG. 9) are preferable to allow the sensor to measure air characteristics accurately.

The sensor housing 200 further may include structural support members (e.g., ring 260), for providing rigidity to the sensor housing 200, and one or more data connectors (e.g., connector 270) for providing the physical interface to the interface 130 between the sensor control system 110 and the sensor module 120. When connecting the sensor module 120 to the data connector 270, internal wires with strain relief (e.g., epoxy-based strain relief) may be used as the connections between the sensor module 120 and the data connector 270.

Figure 6:
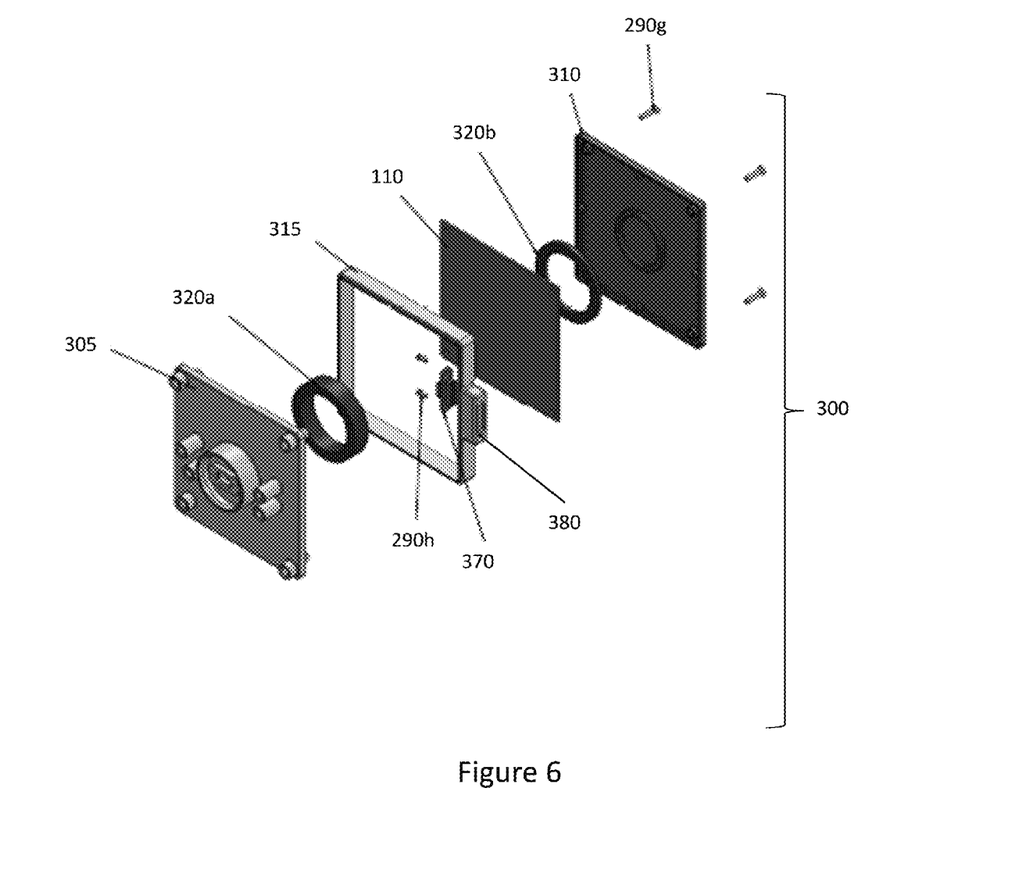
FIG. 6 is an exploded view of a controller housing and sensor control system.

In an embodiment where the sensor control system 110 and the sensor module 120 are split into separate parts, the sensor control module 110 may be built into a separate housing, such as the controller housing 300 shown in FIG. 6. As shown in the exemplary embodiment of FIG. 6, the controller housing 300 may include a number of components that are fastened or screwed together (e.g., using screws 290g and 290h). The controller housing 300 is designed to be mounted on an interior of or on an exterior of the aircraft, such as an RPA. In one such configuration, a sensor mounting plate 305 and an aircraft mounting plate 310 combine together with the enclosure body 315 to form the exterior of the controller housing 300 which is ultimately mounted to the exterior of the aircraft. The sensor control module 110 is then contained within the controller housing 300 and connected to a port connector 370 for passing signals out of the controller housing 300 via the housing data connector 380 (e.g., using any of the external interface types described above). The sensor mounting plate 305 contains or surrounds the data connector 380 for interfacing with the data connector 270 of the sensor housing 200. To reduce vibration on and generally stabilize the sensor control module 110, the controller housing 300 may further include rings 320a and 320b (e.g., rubber o-rings) which are inserted between the sensor mounting plate 305 and the sensor control module 110 and between the sensor control module 110 and the aircraft mounting plate 310, respectively.

The sensor control module 110 in the controller housing 300 may further include additional circuitry such as a real-time clock for performing synchronization with the GPS information, a redundant temperature sensor, non-volatile memory for storage of TRH data and GPS coordinate information, and a non-real-time data transfer connection for post-flight data access. Such a housing may be electrically connected to a SmartNode Pod (or inside a different portion of an aircraft) to receive data from and send control signals to flight control systems, either within the aircraft or external thereto.

Figure 7:
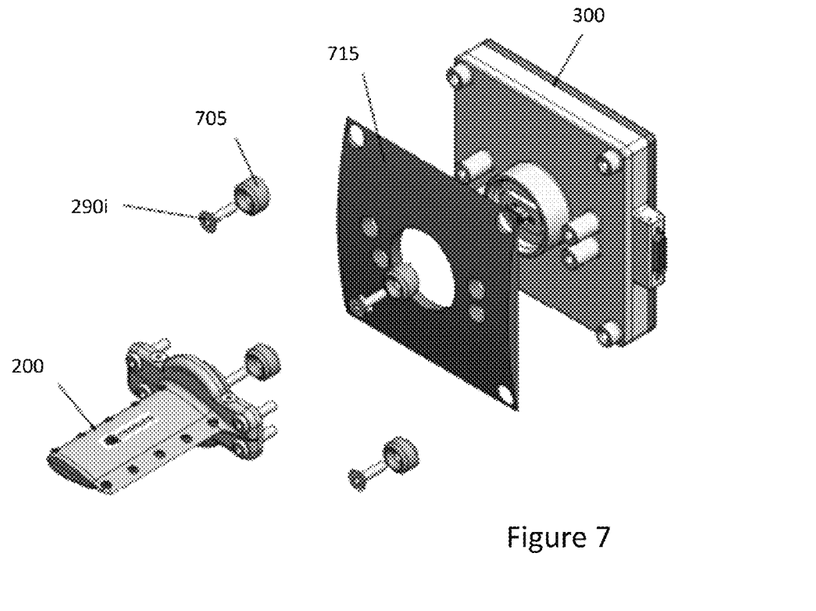
FIG. 7 is an exploded view of portions of the sensor system of FIG. 2.

As shown in FIG. 7, the sensor housing 200 and the controller housing 300 may be fastened together using a number of screws 290i and spacers 705 after connecting the connector of the sensor mounting plate (e.g., a micro-D type connector) with the data connector 270 of the sensor housing 200. By providing a reusable connector on the sensor mounting plate, a number of different sensor modules can be readily exchanged and connected to the controller housing depending on mission parameters and/or sensor modules can be more readily replaced in case of wear and/or damage. In addition, to reduce drag, an additional interface plate 715 may be inserted between the housings 200 and 300. By shaping the interface plate 715 (e.g., using a curved face), the airflow over the controller housing may be reduced.

Using the configurations of FIGS. 2-7, the sensors receive representative air samples to provide a reasonable temperature and humidity, while not interfering with the aerodynamics of the aircraft. The use of redundant sensors on the internally mounted circuit board provides redundancy for sensor information as well as providing the capability to sample data at a fast enough rate to provide data for both asset protection and record weather data throughout an area for improved situational awareness and weather modeling.

In general, the sensor control system 110 runs real-time software on the processor 135 that performs a number of tasks, depending on the sensor module to which it is attached and configuration parameters stored in non-volatile memory electrically connected to the processor 135. The configuration parameters may include, but are not limited to, (1) a system unique ID, (2) communications interface parameters, (3) message rate parameters, (4) message destinations, (5) GPS interface parameters, (6) processing parameters and (7) diagnostic output parameters.

Communications interface parameters may include, but are not limited to, Ethernet configuration related parameters, such as the method of obtaining an IP address (static, DHCP, or link-local) and/or static IP parameters (IP address, net mask, and default gateway).

Message rate parameters may include, but are not limited to, enable/disable flags and message rates (i.e., transmission rates) on a per-type basis for various types of data including, but not limited to, raw data, processed data, and cursor on target (CoT) information. CoT information may further include, but is not limited to, stale time and configurations for individual elements of CoT messages such as dew point, icing intensity, and cloud probability.

Message destination parameters may include, but are not limited to, mode flags (e.g., unicast/multicast flags), destination IP address and port number, and time-to-live (TTL) for multicast) information on a per-type basis for various types of data including, but not limited to, raw data, processed data, and cursor on target (CoT) information.

GPS interface parameters may include, but are not limited to, data source information (e.g., local serial or Ethernet, and Ethernet mode (unicast/multicast)) and UDP multicast group information for multicast reception. Processing parameters may include, but are not limited to, computation method (e.g., mean or median) information for processed data and time window to use for processed data. Diagnostic output parameters may include, but are not limited to flags for enabling/disabling diagnostic output messages, information on a detail level to be used for diagnostic messages, and destination information for diagnostic messages (e.g., mode (unicast/multicast), destination IP and port, and TTL for multicast).

Each of the above exemplary seven types of configuration parameters can be changed over the interface 140 (e.g., Ethernet interface) and stored for use at the next restart. The controller can also be restarted remotely via interface 140 (e.g., by a hardware reset or upon receipt of a "reset" packet) if the change in configuration parameters is to take effect immediately.

When receiving and/or logging temperature, pressure and humidity data from the sensors, the processor 135 processes the data, reformats the data packaged with any externally received GPS information (e.g., across interface 140), if necessary, transmits the data (including error checking) to a designated receiver, and provides a diagnostic interface for displaying logged data and status information. This data is time stamped and transmitted across the external control/data interface 140. The sensor control system 110 further is able to perform sensor health monitoring. In order to provide location context for the temperature and humidity data calculated from the sensor data, the processor 135 receives GPS time and location data (e.g., from an external or internal GPS receiver). In the event that the GPS time and location data is formatted with additional data (e.g., UDP headers), the processor 135 removes or reformats that data as needed to perform the correlation between temperature, pressure and humidity data and the GPS location information. Also, to the extent that a recipient of the data (e.g., a centralized sensor control system) is expecting data be sent back to it in a particular format (e.g., combined TRH data, latitude, longitude, elevation, time, and sensor (GPS and/or TRH) status information) for storage/analysis, the processor 135 performs any data reformatting or packaging (e.g., by adding UDP header information to the TRH and GPS informa-tion) necessary prior to transmission to the recipient. The processor 135 may further store temperature and humidity data to an on-board non-volatile memory interface (e.g., Flash memory or USB-based) for post-flight retrieval.

As discussed above, the sensor control system 110 performs health/integrity testing on the sensors and itself to verify proper operation of the system. In a first embodiment, the processor 135 polls (via the sensor module) the sensors individually and then compares values between sensors and with previously collected data in order to determine a "valid" sensor response. All sensor data is averaged and a single value of temperature and relative humidity are stored for each latitude, longitude, elevation and time step. This data is transmitted to the centralized sensor control system, received by a corresponding external control/data interface, stored in volatile and/or non-volatile memory of a data logging and storage system and sent via a wireless communications device (e.g., a satellite- or earth station-based communication adapter) to ground stations when data links are available. During climb-out on initial ascent and during final recovery descent, data will be stored internally to the sensor control system and can be recovered once data link capability becomes available. This same data transfer scheme is used during data link interruptions in-flight. Alternatively or additionally, the communications device may also include a wired connection for post-flight data downloads. Though the system will report one temperature and relative humidity per location based on this averaging scheme, each of the three individual sensor's information is stored to allow error reporting and to be able to develop an RH gradient useful for asset protection.

A sensor that fails to respond to a measurement request, or that provides a response with an incorrect checksum, is marked as being in an error state. The states of all three sensors, as well as the number of total errors observed for each sensor since power up, are provided to the controller when requested. A sensor in an error state is commanded to soft reset each cycle of the event loop, and polling of that sensor continues as with a healthy sensor. If a sensor returns to providing data correctly, its status is updated to show that it is healthy again, but the total number of errors observed since power up is maintained for diagnostic purposes.

All raw sensor data and all other data sent via the external control/data interface 140 also are archived in the onboard non-volatile memory. Preferably, the data is stored in a FIFO manner such that when the memory is filled, archiving will continue by overwriting the oldest data in the memory. Environmental data stored in the onboard memory can be delivered via the external control/data interface 140 to the centralized sensor control system upon request.

In an alternate embodiment, the processor 135 requests that the sensor module poll each of the sensors and provide to the processor 135 the average sensor data (along with any sensor status information). In such an embodiment, there is reduced communication between the processor 135 and the sensor module 120, thereby enabling processor 135 to perform other functions. Similarly, the sensor module could contain an internal timing circuit and interrupt the processor 135 only when a reading has changed and the time since the last change is at least a configurable amount.

In yet another embodiment, data from the sensor module 120 is stored within the memory of the control module 110 and is sent via platform dependent data-link systems to static IP addresses on the ground. The output data may be delivered using AF standard Cursor-on-Target (CoT) messages through the Falconview (FV) planning system software utilizing an ETHERNET design to both LINUX and Windows PC's. In such a configuration, the information exported by the control module 110 may include a single weather parameter per message as well as the flexibility to send multiple weather data points per latitude/longitude message.

The control module 110 may also perform additional environmental calculations such as the detection of cloud formations and/or icing conditions. Such information may be transmitted along with any sensor data to enable operators to detect dangerous conditions around the aircraft.

While certain configurations of structures have been illustrated for the purposes of presenting the basic structures of the present invention, one of ordinary skill in the art will appreciate that other variations are possible which would still fall within the scope of the appended claims.

The invention claimed is:

1. A sensor system for performing measurement of environmental conditions affecting an aircraft, the sensor system comprising:
   an air foil including an air opening in a bottom surface of the air foil with reference to a direction of airflow across the air foil;
   a screen mounted behind the air opening; and
   at least one environmental condition sensor for sensing an environmental condition in the air having passed through the screen.

2. The sensor system as claimed in claim 1, wherein the at least one environmental condition sensor comprises at least one temperature and relative humidity sensor and at least one pressure sensor.

3. The sensor system as claimed in claim 1, wherein the aircraft is an airplane.

4. The sensor system as claimed in claim 1, wherein the aircraft is a helicopter.

5. The sensor system as claimed in claim 1, wherein the aircraft is a remotely piloted aircraft.

6. The sensor system as claimed in claim 1, wherein the screen comprises an air permeable wire mesh.

7. The sensor system as claimed in claim 1, wherein the at least one environmental condition sensor comprises at least one temperature, pressure and relative humidity sensor.

8. The sensor system as claimed in claim 7, wherein the at least one temperature, pressure and relative humidity sensor comprises three temperature, pressure and relative humidity sensors.

9. The sensor system as claimed in claim 1, further comprising:
   a processor for reading the environmental condition; and
   a memory for storing the environmental condition read by the processor.

10. The sensor system as claimed in claim 9, further comprising a GPS receiver interface for receiving GPS location information corresponding to a location of the sensor system when the environmental condition was read.

11. The sensor system as claimed in claim 9, further comprising an external control/data interface for transmitting the environmental condition read by the processor to a device externally connected to the sensor system.

12. The sensor system as claimed in claim 11, further comprising a GPS receiver interface for receiving GPS location information corresponding to a location of the sensor system when the environmental condition was read, wherein the environmental condition read by the processor is transmitted to the device externally connected to the sensor system along with the location of the sensor system when the environmental condition was read.

13. A sensor system for performing measurement of environmental conditions affecting an aircraft, the sensor system comprising:
   an air foil including an air opening in a bottom surface of the air foil with reference to a direction of airflow across the air foil;
   a screen mounted behind the air opening;
   plural temperature and relative humidity sensors each for sensing the temperature and relative humidity in air having passed through the screen,
   a GPS receiver interface for receiving GPS location information corresponding to a location of the sensor system;
   a processor for reading and averaging sensor values from the plural temperature and relative humidity sensors; and
   a memory for storing averages of the sensor values read by the processor from the plural temperature and relative humidity sensors and the location of the sensor system when the sensor values were read.

14. The sensor system as claimed in claim 13, further comprising an external control/data interface for transmitting the averaged sensor values processed by the processor to a device externally connected to the sensor system.

15. The sensor system as claimed in claim 13, wherein the aircraft is an airplane.

16. The sensor system as claimed in claim 13, wherein the aircraft is a helicopter.

17. The sensor system as claimed in claim 13, wherein the aircraft is a remotely piloted aircraft.

18. The sensor system as claimed in claim 13, wherein the screen comprises an air permeable wire mesh.

19. The sensor system as claimed in claim 13, further comprising:
   plural pressure sensors each for sensing the pressure in the air having passed through the screen.

* * * * *